(12) United States Patent
Price et al.

(10) Patent No.: US 7,145,988 B2
(45) Date of Patent: Dec. 5, 2006

(54) SEALED ELECTRON BEAM SOURCE

(75) Inventors: J. Scott Price, Milwaukee, WI (US); Bruce M. Dunham, Mequon, WI (US)

(73) Assignee: General Electric Company, Schnectady, NY (US)

( * ) Notice: Subject to any disclaimer, the term of this patent is extended or adjusted under 35 U.S.C. 154(b) by 32 days.

(21) Appl. No.: 10/707,284

(22) Filed: Dec. 3, 2003

(65) Prior Publication Data
US 2005/0123096 A1    Jun. 9, 2005

(51) Int. Cl.
*H01J 35/02* (2006.01)
(52) U.S. Cl. .................. 378/141; 378/121; 378/136
(58) Field of Classification Search ................. 378/119, 378/121, 122, 123, 136, 138, 139, 141, 143, 378/140, 161
See application file for complete search history.

(56) References Cited

U.S. PATENT DOCUMENTS

| | | | | |
|---|---|---|---|---|
| 4,119,855 A | * | 10/1978 | Bernacki | ..................... 378/119 |
| 4,188,558 A | * | 2/1980 | Yamamura | ................... 378/121 |
| 4,468,282 A | | 8/1984 | Neukermans | |
| 4,494,036 A | | 1/1985 | Neukermans | |
| 5,241,260 A | * | 8/1993 | Beland | ........................ 378/111 |
| 5,517,545 A | * | 5/1996 | Nakamura et al. | .......... 378/138 |
| 5,612,588 A | | 3/1997 | Wakalopulos | |
| 6,002,202 A | * | 12/1999 | Meyer et al. | ................ 378/161 |
| 6,160,868 A | | 12/2000 | Snyder et al. | |
| 6,192,107 B1 | | 2/2001 | Price et al. | |
| 6,236,713 B1 | | 5/2001 | True et al. | |
| 6,438,208 B1 | * | 8/2002 | Koller | ......................... 378/140 |
| 6,526,122 B1 | * | 2/2003 | Matsushita et al. | ......... 378/138 |
| 6,529,579 B1 | * | 3/2003 | Richardson | ................. 378/141 |
| 6,625,254 B1 | * | 9/2003 | Bachmann et al. | ......... 378/140 |
| 6,674,838 B1 | * | 1/2004 | Barrett | ....................... 378/125 |
| 2003/0021377 A1 | * | 1/2003 | Turner et al. | ................ 378/102 |

FOREIGN PATENT DOCUMENTS

JP         54151384 A   * 11/1979

* cited by examiner

*Primary Examiner*—Edward J. Glick
*Assistant Examiner*—Chih-Cheng Glen Kao
(74) *Attorney, Agent, or Firm*—Peter J. Vogel

(57) ABSTRACT

A sealed electron beam source (12) for an imaging tube (16) is provided. The beam source (12) includes a source housing (50) with a source window (54) having a first voltage potential and a source electrode (52) having a second voltage potential. The source electrode (52) generates electrons and emits the electrons through the source window (54) to a target (32) that is external to the source housing (50). A method of supplying and directing electrons on the target (32) within the imaging tube (16) is also provided. The method includes forming the source housing (50) over the source electrode (52) and sealing the source housing (50). The electrons are generated and emitted from the source electrode (52) and directed through the source window (54) to the target (32).

22 Claims, 2 Drawing Sheets

SEALED ELECTRON BEAM SOURCE

BACKGROUND OF INVENTION

The present invention relates generally to x-ray systems, and more particularly to a method and apparatus for supplying and directing electrons on a target within an imaging tube.

There is a continuous effort to increase x-ray imaging system scanning capabilities. Customers desire the ability to perform longer scans at high power levels. The increase in scan time at high power levels allows physicians to gather images and constructions in a matter of seconds rather than several minutes as with previous x-ray imaging systems. Although the increase in imaging speed provides improved imaging capability, it causes new constraints and requirements for the functionality of the x-ray imaging systems.

X-ray imaging systems include an imaging tube. The imaging tube generates x-rays across a vacuum gap between a cathode and an anode. In order to generate the x-rays, a large direct current (DC) voltage potential is created across the vacuum gap allowing electrons to be emitted from the cathode to a target within the anode. In releasing of the electrons, a filament contained within the cathode is heated to incandescence by passing an electric current therein. The electrons, in the form of an electron beam, are accelerated by the high voltage potential and impinge on the target, whereby they are abruptly slowed down to emit x-rays. The deceleration of the high energy electrons in the target solid produces a large amount of heat.

High-voltage, high power imaging tubes have several disadvantages. High-voltage, high power imaging tubes contain a complex vacuum enclosure that is carefully manufactured to properly prepare internal surfaces and volumes of material enclosed within the imaging tube. Many of the most critical surfaces include a cathode cup and an anode target, which are subject to very high electric field stress. A costly process referred to as "seasoning" prepares the more critical internal surfaces. Seasoning includes removing air from within an imaging tube and heating critical surfaces as well as the imaging tube enclosure, to exhaust any existing gases in the internal surfaces. Seasoning specifications vary between applications due to geometry and material composition differences.

Surfaces exposed to large electromagnetic field gradients must be specially treated due to added stress. Highly stressed surfaces are located within the vacuum enclosure at high discharge locations such as from cathode to anode, anode to frame, and cathode to frame. Any evolution of gas or surface asperity or blemish on any of these surfaces is a precursor to high-voltage activity. High-voltage activity sometimes referred to as "spit" activity, is further described below.

Another disadvantage of imaging tubes is that electric field gradients along with high vapor pressures within the imaging tube can cause high-voltage instability. The electric field gradients are present at an anode target when an electron beam is incident. The high vapor pressures are due to the following gas species: background gas, surface-absorbed gas, target bulk absorbed gas, or track material atoms. Background gas is residual gas remaining in the imaging tube after the exhaust process. Surface-absorbed gas and target bulk absorbed gas refer to gases remaining within surfaces of the imaging tube internal componentry. Track material atoms, refers to atoms on the surfaces that are evaporated into the gases of the imaging tube. The high vapor pressures are at pressures of approximately $10^{-4}$ mbar, which is undesirable compared to preferred operating gas pressure of $10^{-7}$ mbar. The gas species provide ionization targets for incident electron flux. Charged ions and excess electrons produce a low impedance path between high DC potentials of the anode and the cathode. The DC potentials and the electromagnetic field gradients cause spit activity within the imaging tube. Spit activity refers to ignited ions generated by the high-pressured gas that arc to internal surface asperities. Spit activity temporarily causes the x-ray imaging system to malfunction or shutdown, which is especially undesirable during a medical diagnosis.

Also due to the aforementioned and other traditional imaging tube characteristics, the materials and gases used to manufacture the imaging tubes can be limited and extensive. For example, due to backscattering of electrons in traditional imaging tubes, a copper electron collector is used between the cathode and the anode to remove heat. Another limiting example is the inability to use low-Z gases due to increasing vapor pressure during imaging tube use, caused by spit activity and arcing. Low-Z gases can enhance heat transfer between an anode and an imaging tube frame. The limitation of available gases and existing vacuum environment also requires vacuum compatible lubricants for use on anode bearings. The limitation on lubricants limits the ability to produce a more quiet, reliable, and inexpensive anode bearing.

Therefore, it would be desirable to provide an improved method and apparatus for supplying and directing electrons on a target within an imaging tube that eliminates the need for seasoning, provides increased high-voltage stability, and increases imaging system engineering flexibility in choices of materials and gases within an imaging tube.

SUMMARY OF INVENTION

The present invention provides an improved method and apparatus for supplying and directing electrons on a target within an imaging tube. A sealed electron beam source for an imaging tube is provided. The beam source includes a source housing with a source window having a first voltage potential and a source electrode having a second voltage potential. The source electrode generates electrons and emits the electrons through the source window to a target that is external to the source housing.

A method of supplying and directing electrons on the target within the imaging tube is also provided. The method includes forming the source housing over the source electrode and sealing the source housing. The electrons are generated and emitted from the source electrode and directed through the source window to the target.

One of several advantages of the present invention is that it provides a sealed electron beam source for use within an imaging tube that minimizes the need for seasoning the imaging tube. The minimization of seasoning increases time and reduces costs in production of the imaging tube.

Another advantage of the present invention is that due the source electrode being encased and the potential voltage variation between the sealed electron beam source and the target being near zero, high-voltage stability of the imaging tube is increased. The stated features of the present invention also reduce the occurrence of spit activity within the imaging tube.

Furthermore, the present invention provides engineering versatility by allowing the use of various electron source emitter types and low-pressure gases between the sealed electron beam source and the target. The use of low-pressured gases provides increased heat transfer between the anode and the frame of the insert. The increased heat transfer capacity facilitates cooling the target. This improves the heat dissipation rating of the tube thus improving x-ray power output performance.

Moreover, the present invention due to the versatility in fluid types allows for the use of low-pressure lubricants, which in turn allows for inexpensive bearings to be use on a rotating shaft of the anode or on other rotating components within the imaging tube.

The present invention itself, together with attendant advantages, will be best understood by reference to the following detailed description, taken in conjunction with the accompanying figures.

BRIEF DESCRIPTION OF DRAWINGS

For a more complete understanding of this invention reference should now be had to the embodiments illustrated in greater detail in the accompanying figures and described below by way of examples of the invention wherein.

DETAILED DESCRIPTION

Figure 1:
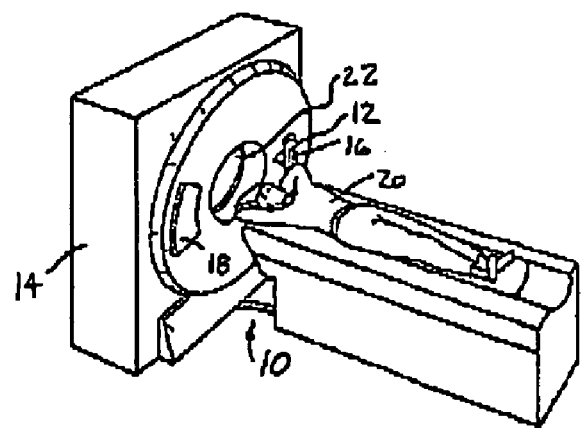
FIG. 1 is a pictorial view example of an imaging system, utilizing a sealed electron beam source in accordance with an embodiment of the present invention.

In each of the following figures, the same reference numerals are used to refer to the same components. While the present invention is described with respect to a method and apparatus for supplying and directing electrons on a target within an imaging tube, the present invention may be adapted to be used in various systems having various modalities including: X-ray systems, radiography systems, angiography systems, cardiography systems, computed tomography systems, or other systems that require the supply and direction of electrons on a target and/or employing more than one of the above systems.

In the following description, various operating parameters and components are described for one constructed embodiment. These specific parameters and components are included as examples and are not meant to be limiting.

Also, in the following description the term "target" may refer to any component within an imaging tube for which electrons are emitted, directed, and impinge thereon. For example, a target may be a surface on a rotating anode, a portion of a window, or a surface within an imaging tube.

Referring now to FIG. 1, a pictorial view example of an imaging system 10, utilizing a sealed electron beam source 12 in accordance with an embodiment of the present invention is shown. The imaging system 10 includes a gantry 14 that has an imaging tube assembly 16 having the beam source 12. The imaging tube 16 projects a beam of x-rays toward a detector array 18. The x-rays after passing through the medical patient 20, within the patient bore 22, are detected and used to create an image. Although, the imaging system 10 is illustrated as a computed tomography system, the imaging system 10 may be any type of imaging system as stated above.

Figure 2:
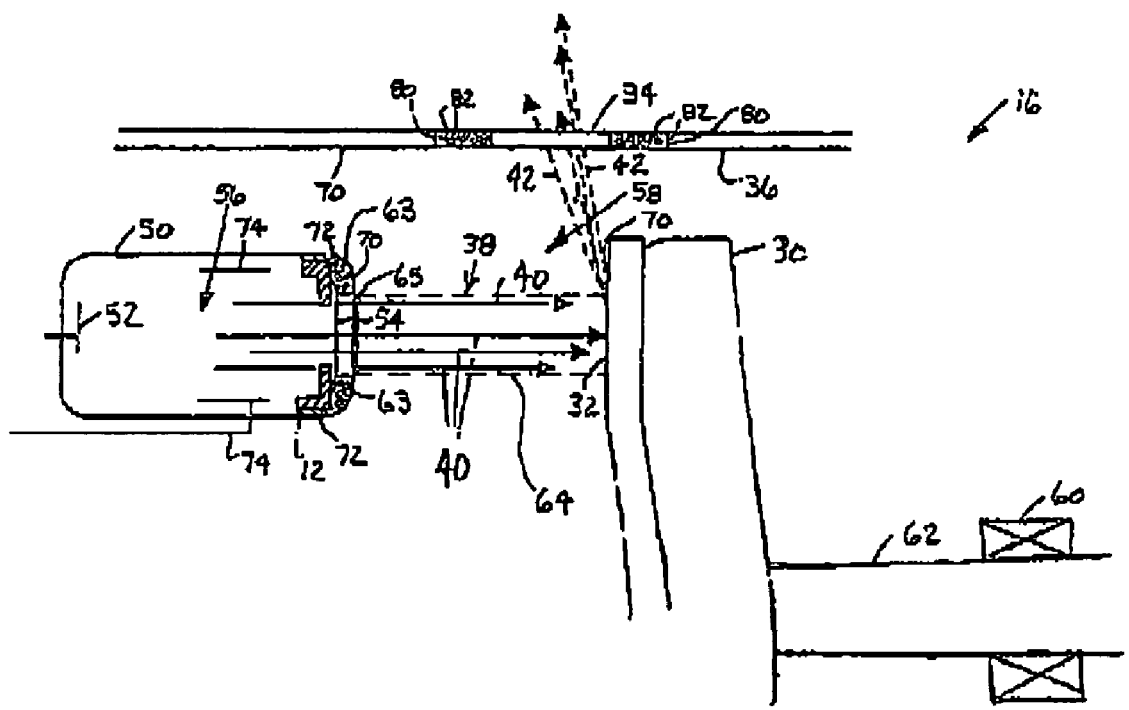
FIG. 2 is a quarter cross-sectional view of an imaging tube in accordance with an embodiment of the present invention.

Referring now to FIG. 2, a quarter cross-sectional view of the imaging tube 16 in accordance with an embodiment of the present invention is shown. The imaging tube 16 includes the beam source 12, an anode 30 having a target 32, and an x-ray window 34 on a frame 36. Electrons are generated and emitted from within the beam source 12 across a gap 38, referred to as an electron beam and represented by arrows 40. The electrons impinge on the target 32 where they are rapidly decelerated to generate x-rays 42, which are passed through the x-ray window 34 for scanning purposes.

The beam source 12 includes a source housing 50, a source electrode 52, and a source window 54. The housing 50 may be formed of glass or other material having similar properties known in the art. Housing 50 is sealed as to separate a source interior 56 from a low-pressured cavity 58, which includes the gap 38. The beam source 12 may be installed in the imaging tube 16 without seasoning, evacuation, or other preparation. In an embodiment of the present invention the beam source 12 is initially aligned, during production of the imaging tube 16, or is adjustable and easily installed and replaced as a sub-assembly to the imaging tube 16. The beam source 12 may be angled towards the target 32 at various angles to increase x-ray production, such as at a glancing angle as known in the art.

Since the beam source 12 is sealed, the low-pressure cavity 58 may be either a vacuum or filled with low-pressured gas to enhance heat transfer between the anode 30 and the frame 36. The low-pressured gas may be any low-Z substance such as helium, nitrogen, argon, or other low-Z substance or a combination thereof. The pressure of the low-pressured gas is adjusted and dependant upon the substance used, as to minimize degradation of the electron beam 40) through scattering of electrons. The use of low-pressured gas also provides for flexibility in types of bearing lubricant that may be used. For example, bearings 60 used on a rotating shaft 62 of the anode 30 do not need to be coated steel balls as used in imaging tube applications that are exhausted to create a vacuum, but rather may be bearings having other types of coatings known in the art.

The source electrode 52 may be a thermionic tungsten wire coil to emit electrons or it may contain a field emitter array made of Spindt cones, barrel, or hollow cylinders. The source electrode 52 may also contain carbon nanotubes, photoemitters, or other electron emitters known in the art. In an example embodiment of the present invention a source electrode having a variable voltage potential is used to increase usefulness of the source electrode for multiple imaging systems where focal spot variability is necessary.

The source window 54 is formed from a silicon (Si) material. The source window 54 is thin and therefore transmits a large percentage of the approximately 80 kV to 120 kV incident electron beam with little electron beam loss and accompanying heating at the source window 54. Some energy is deposited at the source window 54 and cooling is provided using methods known in the art. An example of a type of cooling that may be used is monolithic cooling, which includes coolant feedthroughs 63 in the source window 54. Source window 54 allows most of the electron emission, from the source electrode 52, to pass through the source window 54 and to the anode 30. On the other hand, the source window 54 prevents indirect electron emission from passing through the source window 54. In so doing, the source window 54 prevents off-axis or scattered electrons, which generate less energy when impinging upon the target 32 than electrons that are on-axis in a focal track 64 that have full energy, from escaping the beam source 12. In other words the source window 54 suppresses off-focal radiation by containing the off-axis electrons within the beam source 12. A momentum selecting static magnetic field may also be used within the beam source 12 to further preferentially deflect low momentum electrons away from the focal track 64.

Since energy deposition in thicker layers of material is higher than thin layers, a thick layer of protective material 65 may be installed on the source window 54 to protect the window 54 during manufacturing and assembly processes. The protective layer may also be formed from Si or other similar material known in the art. The protective layer may then be removed upon installation by operating the imaging tube and allowing the electron beam 40 to pass through the thin layer and melt the protective layer.

The source housing 50, the frame 36, and the source window 54 have the ability to extract heat from backscattered electrons, which allow the beam source 12, the frame 36, and the window 54 to be used as an electron collector. This is advantageous, since backscattered electrons are not concentrated in one spot or surface due to potential differences therein. In particular, the target 32 does not attract backscattered electrons, which in turn produces x-radiation that escapes the window 34. X-radiation is undesirable because it contributes to image noise that can lower contrast-to-noise ratio of the system 10, which is a measure of image quality. This aspect is further advantageous since the total power in the backscattered electrons is distributed over a larger area, thus, lowering the average incident power density, measured in kW/unit area. Lowering of the average incident power density eases engineering of heat extraction.

Also, since highly different potential surfaces such as the source electrode 52 and the source window 54 are contained within the beam source 12, the probability of arcing across particles within the cavity 58, is unlikely. For example, the source electrode 52 may be at a voltage potential of 100 kV as compared with the source window 54, the frame 36, and the target 32, which are at a voltage potential approximately equal to ground. Therefore, although the electrons are initially emitted towards the target 32, due to the voltage potential between the source electrode 52 and the source window 54, the electrons experience minimal potential differences in the cavity 58. The minimal potential differences diminish the likelihood for arcing.

The anode 30 may be a stationary or rotating anode having the target 32. The target 32 has approximately the same voltage potential as the source window 54. Since there is no high electromagnetic field gradient present at the target 32 and other internal surfaces 70, as in traditional imaging systems, seasoning of the internal surfaces 70 within the imaging tube 16 is minimized. Other internal surfaces 70 may include an internal surface of the frame 36 or an exterior surface of the beam source 12, as well as others. Reduction of the electric field gradients also reduces the incidence of spit activity.

A grid 72 and focusing electrodes 74 may be used to further focus electrons onto the target 32 as known in the art. Grid 72 and the electrodes 74 are positioned between the source electrode 52 and anode 30 and may be internal or external to the beam source 12. The grid 72 and the electrodes 74 may be of various type, style, size, and shape. Grid 72 and the electrodes 74 may also have various voltage potential levels corresponding to a predetermined desired focusing level.

The frame 36 and the anode 30 may be cooled using methods known in the art. The frame 36 and the anode 30 may have a coolant channel housing 80 having a coolant channel 82, with coolant flowing therein. The coolant absorbs and removes heat from the frame 36 and the anode 30. The coolant channel 82 may be fluidically coupled to the coolant feedthroughs 63. The coolant therefore cooling the target 32 and both windows 34 and 54. The coolant channel housing 80 is meant to be an illustrative example, other cooling methods know in the art may be used. Since the electrons essentially follow a straight path, due to non-existence of an electric field, the amount of cooling is minimized or potentially non-essential depending upon the application.

Figure 3:
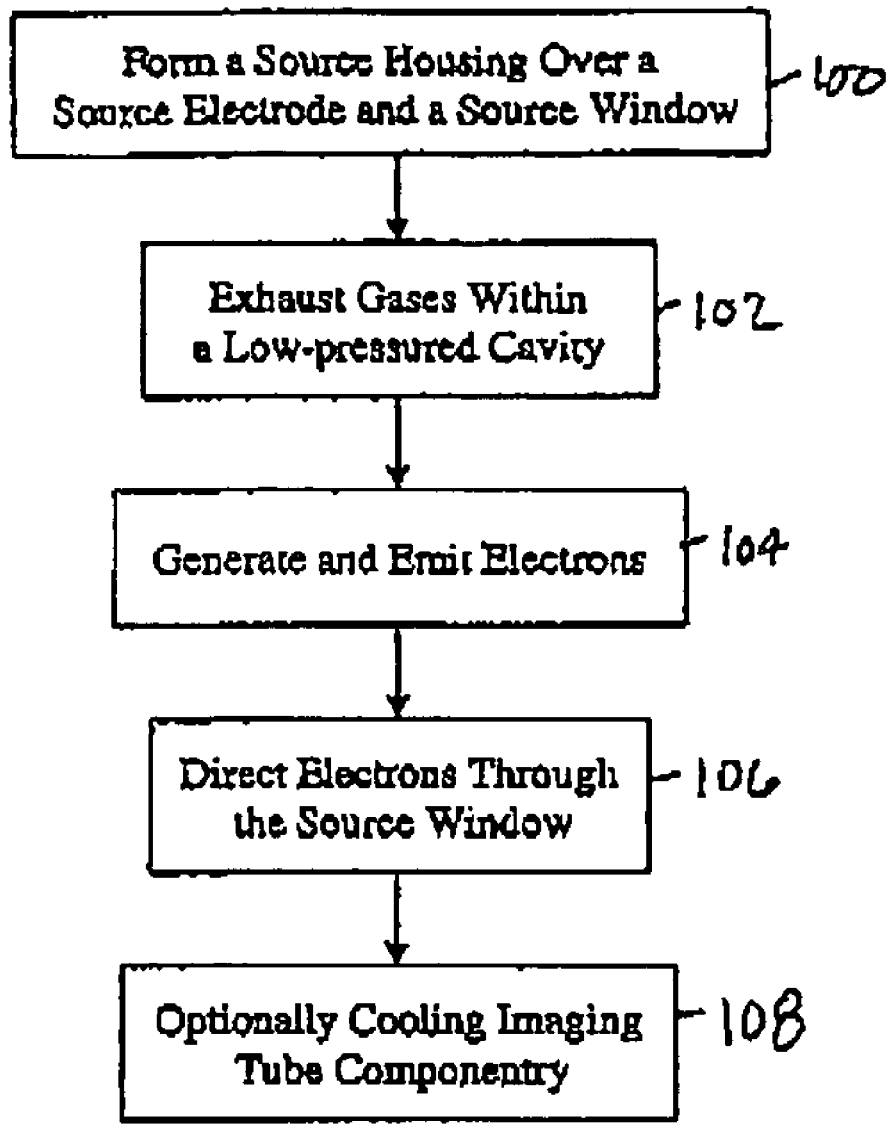
FIG. 3 a logic flow diagram illustrating a method of supplying and directing electrons on a target within an imaging tube in accordance with an embodiment of the present invention.

Referring now to FIG. 3, a logic flow diagram illustrating a method of supplying and directing electrons on the target 32 within the imaging tube 16 in accordance with an embodiment of the present invention is shown.

In step 100, the source housing 50 is formed over the source electrode 52 and the source window 54. The source housing 50 is formed using methods known in the art and is sealed to isolate the source interior 56 from cavity 58.

In step 102, spurious gases existing in the cavity 58 are exhausted to create a vacuum. Optionally, low-pressured gases, as stated above, are injected into the cavity 58 to enhance heat transfer between the target 32 and the frame 36.

In step 104, the beam source 12 generates and emits electrons from the source electrode 52 to impinge on the target 32 and generate the x-rays 42 that are directed through the x-ray window 34.

In step 106, the source window 54 allows direct electron emission to pass through the source window 54 and prevents indirect electrons or scattered electrons from passing through the source window 54. In so doing, directing electrons through the source window 54, in an in-line path to the target 32.

In step 108, the source housing 50, the frame 36, the anode 30, or other internal imaging tube componentry may be optionally cooled via the coolant channel housing 80 and the feedthroughs 63 as described above or by other methods known in the art.

The present invention provides improved high-voltage stability, since an imaging tube frame, source window, and anode target are all at approximately ground potential, thereby reducing the production of arcs and spit activity within an imaging tube. This is especially important in cardiac imaging systems where the time of a patient subjected to contrast media is limited and motions of internal organs of the patient are critical. The present invention reduces production time in manufacturing of imaging tubes by minimizing the need for seasoning. The above stated advantages increases lifetime of imaging tubes and decreases costs and time involved in production of the imaging tubes. Also, other sub-component designs may be incorporated, such as different bearing lubricant, to further increase durability and lifetime of the imaging tubes.

The above-described apparatus, to one skilled in the art, is capable of being adapted for various purposes and is not limited to the following systems: X-ray systems, radiography systems, angiography systems, cardiography systems, ultrasound systems, nuclear imaging systems, computed tomography systems, or other systems that require the supply and direction of electrons on a target. The above-described invention may also be varied without deviating from the spirit and scope of the invention as contemplated by the following claims.

The invention claimed is:

1. A sealed electron beam source for an imaging tube comprising:
   a source housing comprising;
      a non-apertured source window forming a sealed structure, that separates a source interior from an external vacuum cavity, with said source housing and having a first voltage potential; and a source electrode having a second voltage potential and generating electrons, said source electrode emitting said electrons through said source window to a target external to said source housing and internal to the imaging tube;

wherein said source window comprises feedthroughs for a coolant to flow therein and absorb heat from said source window.

2. A source as in claim 1 further comprising:

a coolant channel housing thermally coupled to and at least partially defined by said source housing comprising;

a coolant channel; and said coolant flowing therein, said coolant absorbing heat from said source housing.

3. A source as in claim 1 wherein said source window allows direct electron emission to pass through said source window to said target and prevents indirect electron emission from passing through said source window.

4. A source as in claim 1 wherein said source electrode comprises at least one of a thermionic tungsten wire coil, a field emitter array, or a photoemitter.

5. A source as in claim 1 wherein said source electrode is a focusing electrode.

6. A source as in claim 1 wherein said source electrode has a variable potential.

7. A source as in claim 1 further comprising a grid coupled between said source electrode and said target, said grid focusing said electrons.

8. A source as in claim 7 wherein said grid is coupled within said source housing.

9. A source as in claim 1 wherein the sealed electron beam source is a complete and separate sub-assembly of an imaging tube.

10. A source as in claim 1 wherein said first voltage potential is approximately equal to a third voltage potential of said target.

11. An imaging tube comprising:

a rotating target having a third voltage potential and decelerating electrons to generate x-rays within the imaging tube; and a sealed electron beam source external, separate, and sealed from said target and separating a source interior from a vacuum cavity containing said rotating target comprising;

a source housing comprising;

a source window having a first voltage potential that is approximately equal to said third voltage potential; and a source electrode having a second voltage potential and generating said electrons, said source electrode emitting said electrons through said source window to said target.

12. An imaging tube as in claim 11 further comprising:

a coolant channel housing thermally coupled to and at least partially defined by said source housing comprising;

a coolant channel; and a coolant flowing therein, said coolant absorbing heat from said source housing.

13. An imaging tube as in claim 11 further comprising:

a frame coupled within the imaging tube;

said vacuum cavity fluidically coupled between said frame and said target, and at least partially defined by said frame, said target, and said sealed electron beam source;

said vacuum cavity is at least partially exhausted or filled with a low-pressure gas.

14. An imaging tube as in claim 13 wherein said low-pressure gas comprises at least one of a low-Z substance, helium, nitrogen, or argon.

15. An imaging tube as in claim 11 wherein said sealed electron beam source is directed at said target at a glancing angle.

16. An imaging tube as in claim 11 wherein said source window allows direct electron emission to pass through said source window to said target and prevents indirect electron emission from passing through said source window.

17. An imaging tube as in claim 11 further comprising:

a frame;

an x-ray window coupled to said frame; and a coolant channel housing coupled to said frame and cooling said x-ray window.

18. An imaging tube as in claim 17 wherein said source window comprises feedthroughs and said coolant channel housing comprises coolant channels that are fluidically coupled to said feedthroughs.

19. A method of supplying and directing electrons on a target within an imaging tube comprising:

forming a source housing over a source electrode;

sealing the source housing from an external vacuum cavity that is within the imaging tube;

forming said vacuum cavity comprising said source housing and the target;

at least partially filling said vacuum cavity with a low-pressure gas;

generating and emitting electrons from said source electrode; and directing said electrons through a source window to the target.

20. A method as in claim 19 wherein directing said electrons through a source window further comprises:

allowing direct electron emission to pass trough said source window; and preventing indirect electrons from passing through said source window.

21. A method as in claim 19 further comprising cooling said source housing via a coolant channel housing.

22. A method as in claim 19 further comprising utilizing said low-pressure gas to enhance heat transfer between the target and a frame of the imaging tube.

* * * * *